(12) United States Patent
Martin et al.

(10) Patent No.: US 9,823,237 B2
(45) Date of Patent: Nov. 21, 2017

(54) INTEGRATED BREATH ALCOHOL SENSOR SYSTEM

(71) Applicant: Automotive Coalition for Traffic Safety, Inc., Washington, DC (US)

(72) Inventors: Hans Göran Evald Martin, Delsbo (SE); Henrik Rödjegård, Nasviken (SE); Jan-Åke Henning, Hudiksvall (SE); Pavel Zyrianov, Delsbo (SE)

(73) Assignee: Automotive Coalition for Traffic Safety, Inc., Washington, DC (US)

( * ) Notice: Subject to any disclaimer, the term of this patent is extended or adjusted under 35 U.S.C. 154(b) by 0 days.

(21) Appl. No.: 15/090,948

(22) Filed: Apr. 5, 2016

(65) Prior Publication Data
US 2016/0356764 A1 Dec. 8, 2016

Related U.S. Application Data

(60) Provisional application No. 62/171,566, filed on Jun. 5, 2015.

(51) Int. Cl.
| | |
|---|---|
| *G01J 5/02* | (2006.01) |
| *G01N 33/497* | (2006.01) |
| *G01N 21/3504* | (2014.01) |
| *G01N 21/31* | (2006.01) |
| *G01N 33/00* | (2006.01) |
| *G01N 21/03* | (2006.01) |
| *G01N 21/15* | (2006.01) |

(52) U.S. Cl.
CPC ....... *G01N 33/4972* (2013.01); *G01N 21/314* (2013.01); *G01N 21/3504* (2013.01); *G01N 33/004* (2013.01); *G01N 33/0026* (2013.01); *G01N 21/031* (2013.01); *G01N 21/0332* (2013.01); *G01N 2021/158* (2013.01); *G01N 2021/3196* (2013.01); *G01N 2201/068* (2013.01); *G01N 2201/128* (2013.01)

(58) Field of Classification Search
CPC .......................... G01N 33/483; G01N 33/497
See application file for complete search history.

(56) References Cited

U.S. PATENT DOCUMENTS

| | | | |
|---|---|---|---|
| 5,971,937 A * | 10/1999 | Ekstrom | ............ G01N 33/4972 422/84 |
| 6,468,222 B1 | 10/2002 | Mault et al. | |
| 2004/0093957 A1 | 5/2004 | Buess et al. | |
| 2008/0228098 A1 | 9/2008 | Popov et al. | |
| 2009/0039267 A1 | 2/2009 | Arndt et al. | |
| 2011/0283770 A1* | 11/2011 | Hok | ..................... A61B 5/0059 73/23.3 |
| 2011/0302992 A1 | 12/2011 | Robbins et al. | |

FOREIGN PATENT DOCUMENTS

| | | | | |
|---|---|---|---|---|
| AU | WO 9222813 A1 * | 12/1992 | ......... G01N 33/4972 |
| DE | 10-2011106410 | 8/2012 | |

* cited by examiner

*Primary Examiner* — Kiho Kim
(74) *Attorney, Agent, or Firm* — Pandiscio & Pandiscio

(57) ABSTRACT

Systems, apparatus and methods determine the presence of a volatile substance in expired breath. Alcohol concentrations can be determined from expired breath through the use of electromagnetic detection. The systems, apparatus and methods allow measurements of volatile substances to be done accurately and quickly over a wide range of temperatures, and are easily incorporated into vehicles.

46 Claims, 18 Drawing Sheets

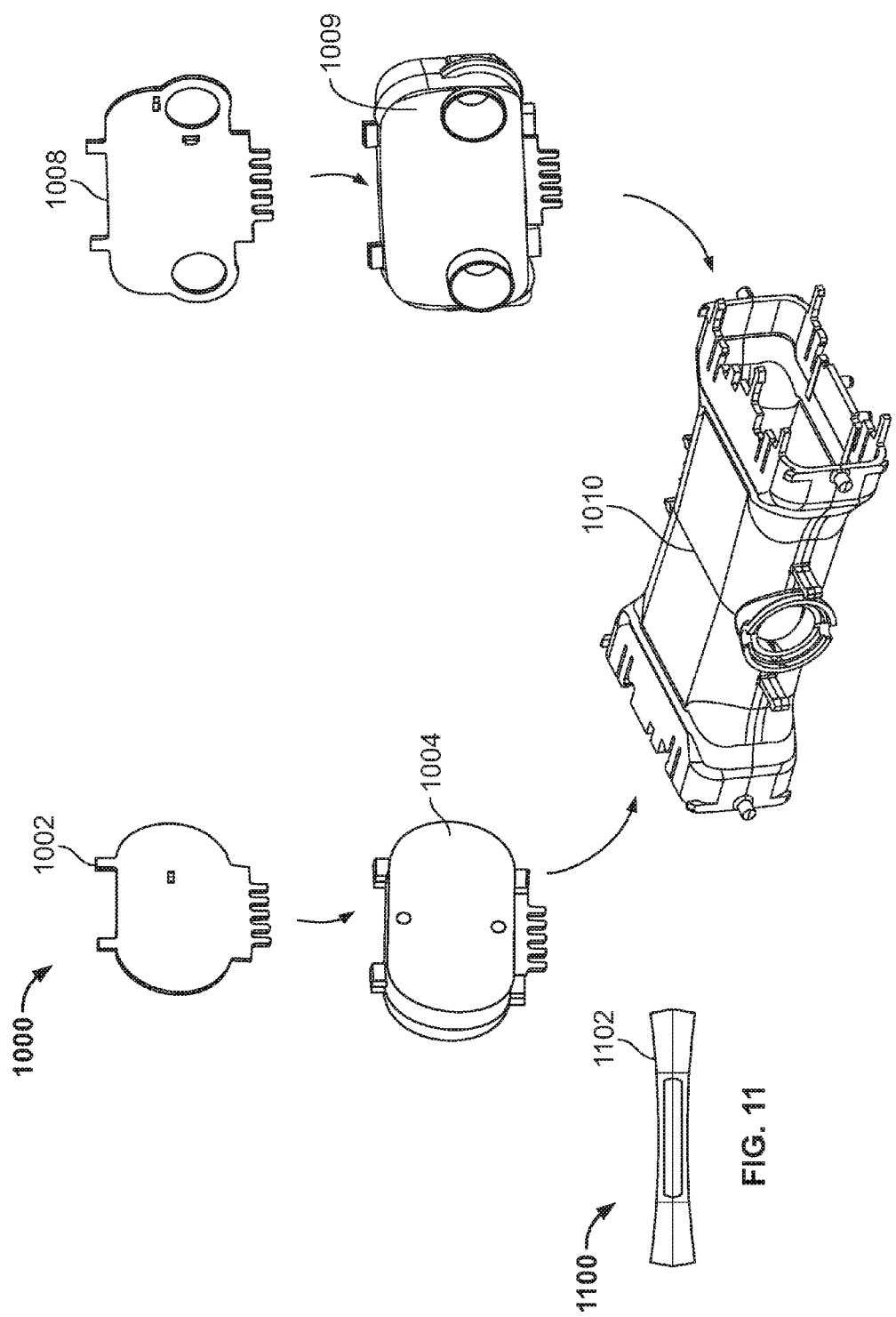

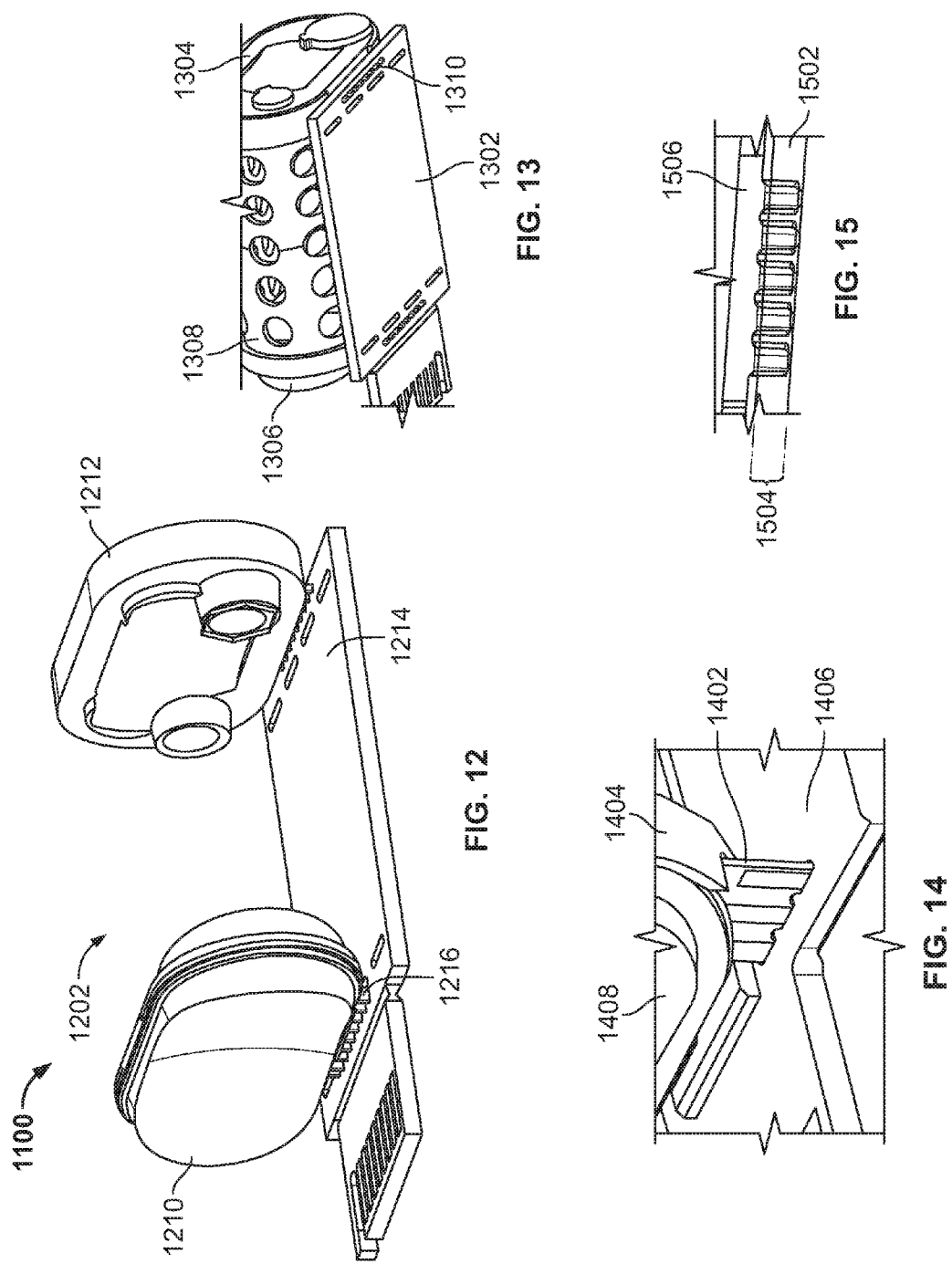

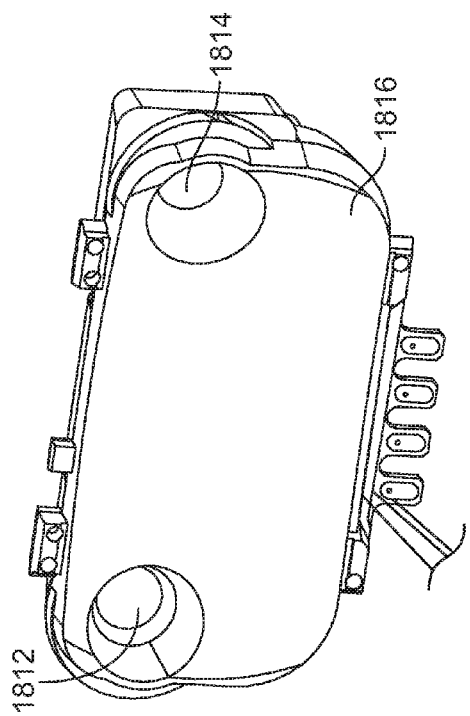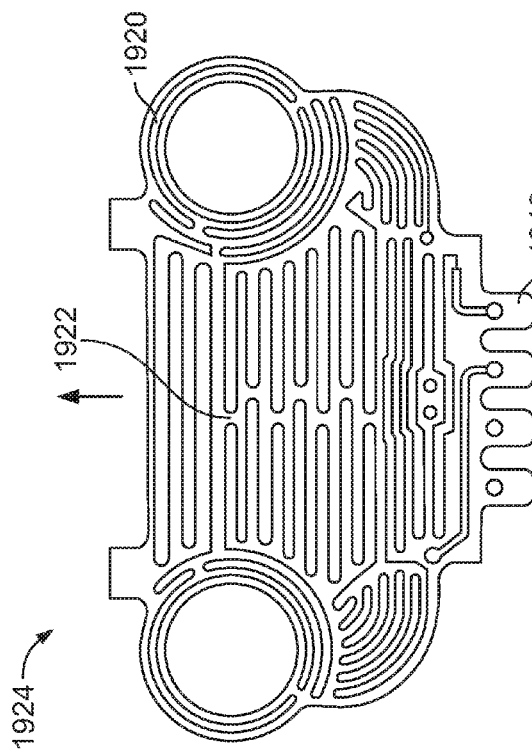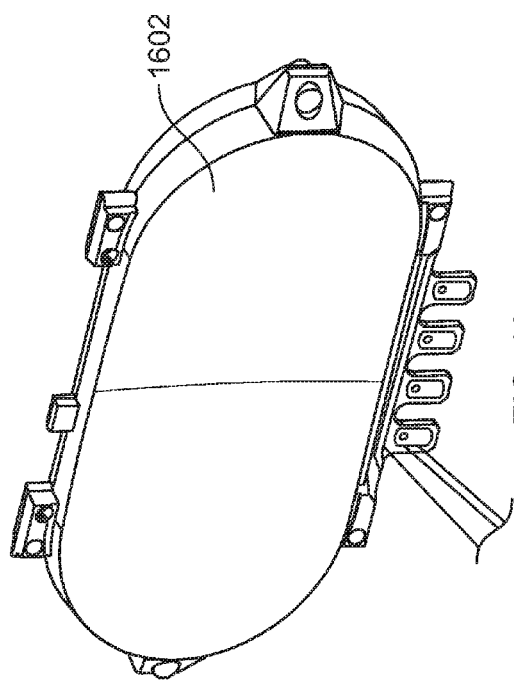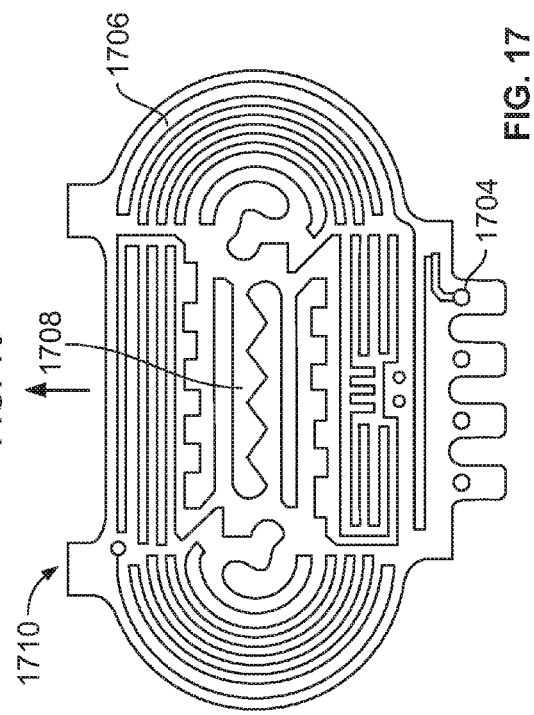

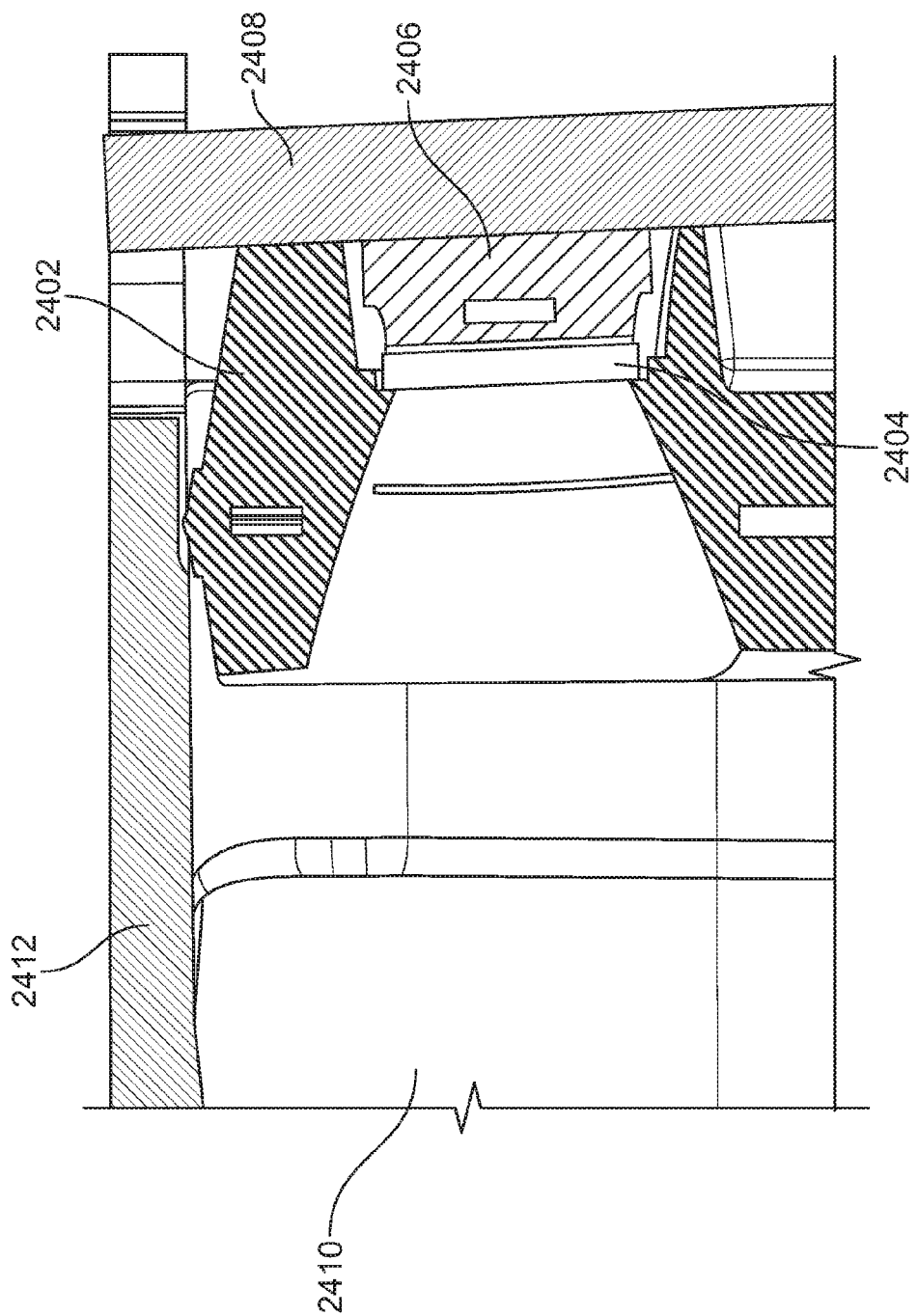

INTEGRATED BREATH ALCOHOL SENSOR SYSTEM

CROSS REFERENCE TO RELATED APPLICATION

This claims the benefit of, commonly-assigned U.S. Provisional Patent Application No. 62/171,566, filed Jun. 5, 2015, which is hereby incorporated by reference herein in its entirety.

STATEMENT REGARDING FEDERALLY SPONSORED RESEARCH OR DEVELOPMENT

This invention was made with Government support under contract number DTNH22-08-H-00188 awarded by the National Highway Traffic Safety Administration. The government has certain rights in this invention.

BACKGROUND OF THE INVENTION

The present invention generally relates to systems, apparatus and methods for the determining of the presence of a volatile substance in expired breath. In particular, the systems, apparatus and methods are designed to provide measurements of volatile substances, such as alcohol in blood, quickly and accurately under a wide range of environmental temperatures based on concentrations of the volatile substances in breath.

A number of existing methods to determine alcohol concentration in expired air are described in the literature. These include, for example, catalytic semiconductors, fuel cells and infrared spectroscopy. Infrared (IR) spectroscopy makes use of the specific "finger print" that gas-phase alcohol produces when illuminated by infrared light to determine alcohol concentration. The absorption spectrum of any substance is due to resonant molecular vibrations, which are specific to the atomic bonds within a molecule or compound. From this absorption spectrum, the specific substances and their absolute or relative concentrations within a tested gas or sample can be determined. This technique is highly selective between substances.

The performance of breath-based alcohol sensors is often noted with respect to accuracy over a certain range of measurement. For evidentiary instruments, accuracy of ±5% is frequently required, whereas ±20% is considered adequate for screening and similar purposes. Sensors for the consumer market have lower accuracy. Among these and screening instruments, systematic error caused by the poorly controlled condition of the tested breath is common. For IR-based instruments, systematic errors can be minimized by a calibration procedure with sample gases whose temperature and water moisture mimic expired breath and contain known concentrations of ethanol or other volatile substances of interest. The remaining error behaves as stochastic noise from the sensor signal or signals.

SUMMARY

The systems, apparatus and methods described herein measure volatile substance concentrations in breath. In particular, the systems, apparatus and methods are designed to be incorporated into a vehicle and to provide measurements of volatile substances, such as alcohol in blood, quickly and accurately under a wide range of environmental temperatures based on concentrations of the volatile substances in breath.

In an example of a breath alcohol sensor, there is provided an inlet for taking in air from the surrounding environment. The air is then preheated to an operating temperature of the breath sensor by a preheater, after which it is circulated into a detection cavity enclosed in a tube cell. The detection cavity contains two detection paths, one of which senses a tracer gas indicating the degree of breath dilution, and the second of which senses the volatile substance of interest. These two detection paths are arranged to allow for a smaller footprint of the breath sensor and substantially simultaneous measurements of the airflow. Logic in signal communication with each sensing path then determines a concentration of the volatile substance in the exhaled breath. The emitters and detectors that comprise elements of the first and second signal paths are thermally isolated and the breath sensor as a whole is substantially maintained at a single operating temperature. In some embodiments, the two detection paths may be perpendicular, and in other embodiments, the two detection paths may be collinear.

Another example of a breath alcohol sensor includes an inlet for taking in air from the surrounding environment. The air is then preheated to an operating temperature of the breath sensor by a preheater, after which it is circulated into a detection cavity enclosed in a tube cell. The tube cell and detection cavity is then further enclosed by a housing case such that there is a gap between the external wall of the tube cell and the interior wall of the housing case. The detection cavity contains two detection paths, one of which senses a tracer gas indicating the degree of breath dilution, and the second of which senses the volatile substance of interest. These two detection paths allow for a smaller footprint of the breath sensor and substantially simultaneous measurements of the airflow. In some embodiments, the two detection paths may be perpendicular, in other embodiments, the two detection paths may be collinear.

Logic in signal communication with each sensing path then determines a concentration of the volatile substance in the exhaled breath. The emitters and detectors that comprise elements of the first and second signal paths are thermally isolated and the breath sensor as a whole is substantially maintained at a single operating temperature. Thermal equilibrium of the breath sensor may be further ensured by a fan, pump, or other device which re-circulates the airflow in the gap between the housing case and the tube cell over the breath sensor.

BRIEF DESCRIPTION OF THE DRAWINGS

Further features of the subject matter of this disclosure, its nature and various advantages, will be apparent upon consideration of the following detailed description, taken in conjunction with the accompanying drawings, in which like reference characters refer to like parts throughout, and in which:

FIG. 10 depicts two perspective views of a first mirror, two perspective views of a second mirror, and their relative positions to the tube cell in addition to built in heating elements underneath the reflective surface of each mirror, according to an illustrative implementation;

FIG. 11 depicts a perspective view of a first mirror, according to an illustrative implementation;

FIG. 12 depicts a perspective view of a connection between the mirrors and a backplane surface, according to an illustrative implementation;

FIG. 13 depicts a perspective view of the connection between the mirrors, tube cell a backplane surface, according to an illustrative implementation;

FIG. 14 depicts a tooth connection between a mirror and a backplane surface, according to an illustrative implementation;

FIG. 15 depicts a tooth connection between a mirror and a backplane surface, according to an illustrative implementation;

FIG. 16 depicts a perspective view of a mirror, according to an illustrative implementation;

FIG. 17 depicts the distribution of heating elements in a mirror, according to an illustrative implementation;

FIG. 18 depicts a perspective view of a mirror, according to an illustrative implementation;

FIG. 19 depicts the distribution of heating elements in a mirror, according to an illustrative implementation;

FIG. 24 depicts a cross sectional view of an incorporation of the volatile substance detector into a mirror, according to an illustrative implementation;

DETAILED DESCRIPTION

Gas exchange between pulmonary capillary blood and alveolar air exhibits highly efficient equilibrium kinetics, making the measurement of breath concentrations of certain substances accurate indicators of their corresponding blood concentrations. In particular, breath alcohol concentrations have been shown to closely track blood alcohol concentrations, and the conversion factor between the two can be standardized. Breath alcohol concentration (BrAC) is related to blood alcohol concentration (BAC) by the approximate conversion equation BrAC[mg/l]=0.5*BAC[mg/g]. Other analytes of interest besides ethanol, or EtOH, will have different breath to blood conversion coefficients. The non-invasive nature of BrAC measurements, as opposed to the need for drawing blood in direct BAC measurements, makes breath-based systems for alcohol detection appealing for general commercial use.

Breath-based alcohol measurement systems integrated into commercial vehicles suffer from a number of challenges unique to the limitations and variability of conditions in a consumer vehicle. These systems should be able to reach a constant and controllable operation temperature under a wide range of environmental conditions and temperatures, and should achieve this within a short start-up time to prevent inconvenience to sober drivers. A related issue is the need to prevent condensation build-up on detection surfaces because of contact between warm, moist breath and cooler surfaces. Other design considerations for easy integration into a vehicle include minimizing the footprint of the device so that it is conveniently accessible to the driver and will not disturb normal vehicle operation. If the device uses IR spectroscopy, in which signal strength is a direct function of the path length of the detected light, a number of engineering solutions would be used to meet this geometric constraint while ensuring a high resolution signal. Furthermore, the sensor should be energy efficient with low power demands, and relatively cheap and easy to produce, all without sacrificing accuracy.

To provide an overall understanding of the disclosure, certain illustrative implementations will now be described, including systems and methods for providing a breath sensor for measuring blood alcohol.

Figure 1:
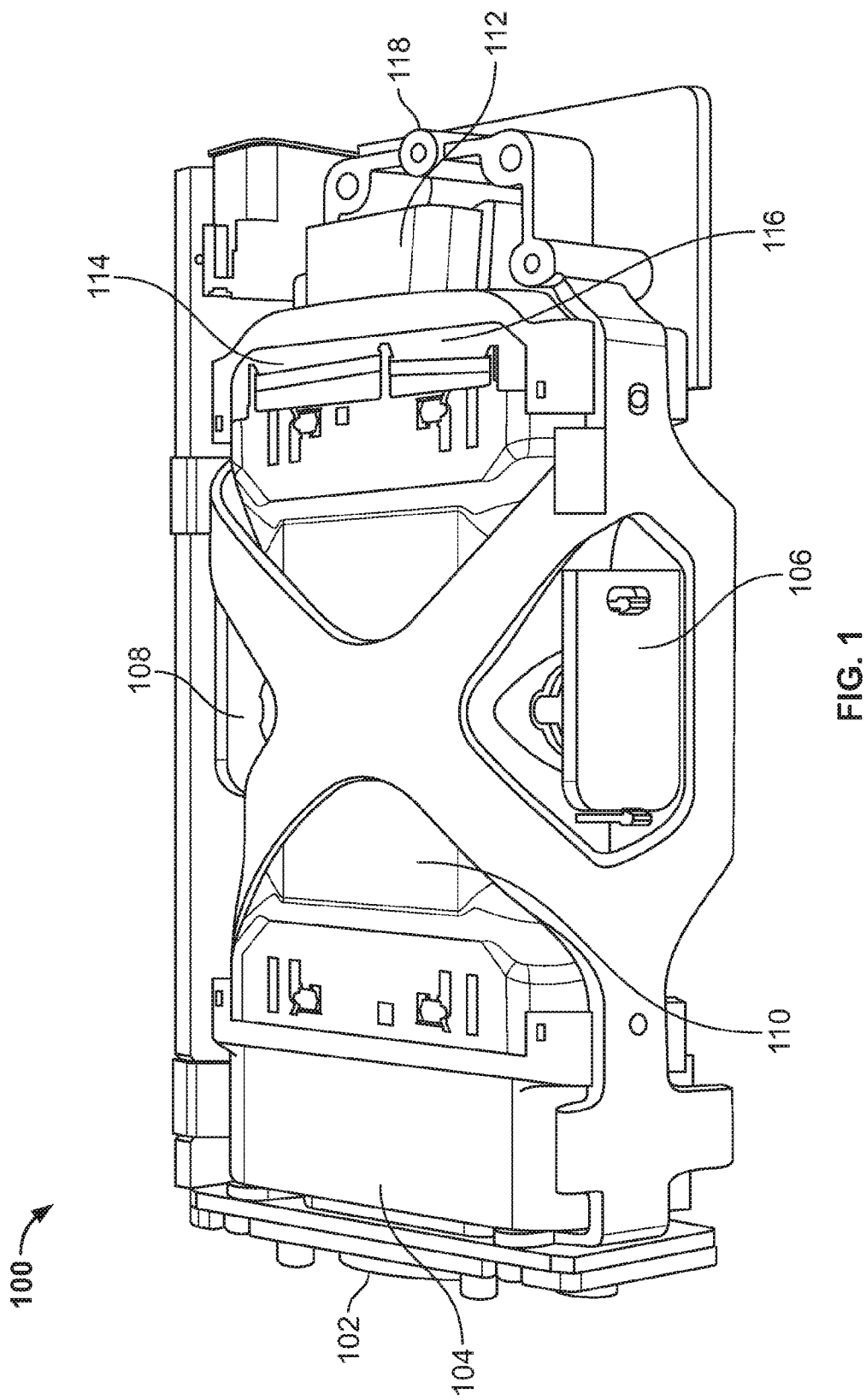
FIG. 1 depicts a perspective view of a breath sensor according to an illustrative implementation of the present invention.

FIG. 1 is a perspective drawing of an illustrative breath sensor according to an implementation of the present invention. As shown in FIG. 1, air from outside of the detector 100 enters through an air inlet 102, and may then be heated to an operating temperature of the device by a preheater 104. The operating temperature is typically different from a temperature outside of the breath sensor. In some implementations, the operating temperature is substantially higher than the temperature outside of the detection cavity. In an example where the breath sensor is integrated into a vehicle, the vehicle operating temperature, and thus the temperature of ambient air outside of the device, may be in a range from −40° C. to 85° C. The dew point for exhaled air is approximately 32° C. The operating temperature may be set to be higher than the ambient temperature and also higher than the dew point, plus an extra temperature control margin of about +10° C. The operating temperature may thus be greater than 45° C. The operating temperature may simplify thermal control of the breath sensor by allowing all temperature controllers to be heaters, as opposed to including both heating and cooling functions. The preheated air then enters a detection cavity connected to the inlet 102 and enclosed by a tube cell 110. The tube cell 110 is connected to a first electromagnetic emitter 108 and a first electromagnetic detector 106, which together comprise the first detection path that passes through the detection cavity. In one implementation, the first detection path selectively tests for absorption of $CO_2$. The selectivity of the detector for $CO_2$ is typically performed by detecting mid-wavelength infrared (MID IR) with an optical bandpass filter specified by, for example, CWL=4.26 μm/FWHM=0.15 μm to obtain 100% spectral selectivity for $CO_2$. Typically, there is no interference with any other relevant gas. The emitter 108 and detector 106 may be interchanged and their positions are not limited to this particular arrangement. The second detection path includes a second detector 114 and a second emitter 116, both located at the end of the tube cell opposite the inlet 102. In one implementation, the second detection path selectively tests for a volatile substance of interest (e.g. alcohol). The air flow then leaves the detection cavity through an air outlet 116. As shown in FIG. 1, the breath sensor 100 may optionally include a fan 112 or other mechanism which actively transports air from the inlet 102 through the tube cell 110 and detection cavity, and out through the outlet 118. All physical components are designed to be symmetrical to avoid tensions in the breath sensor and to improve thermal gradients across the breath sensor.

Figure 2:
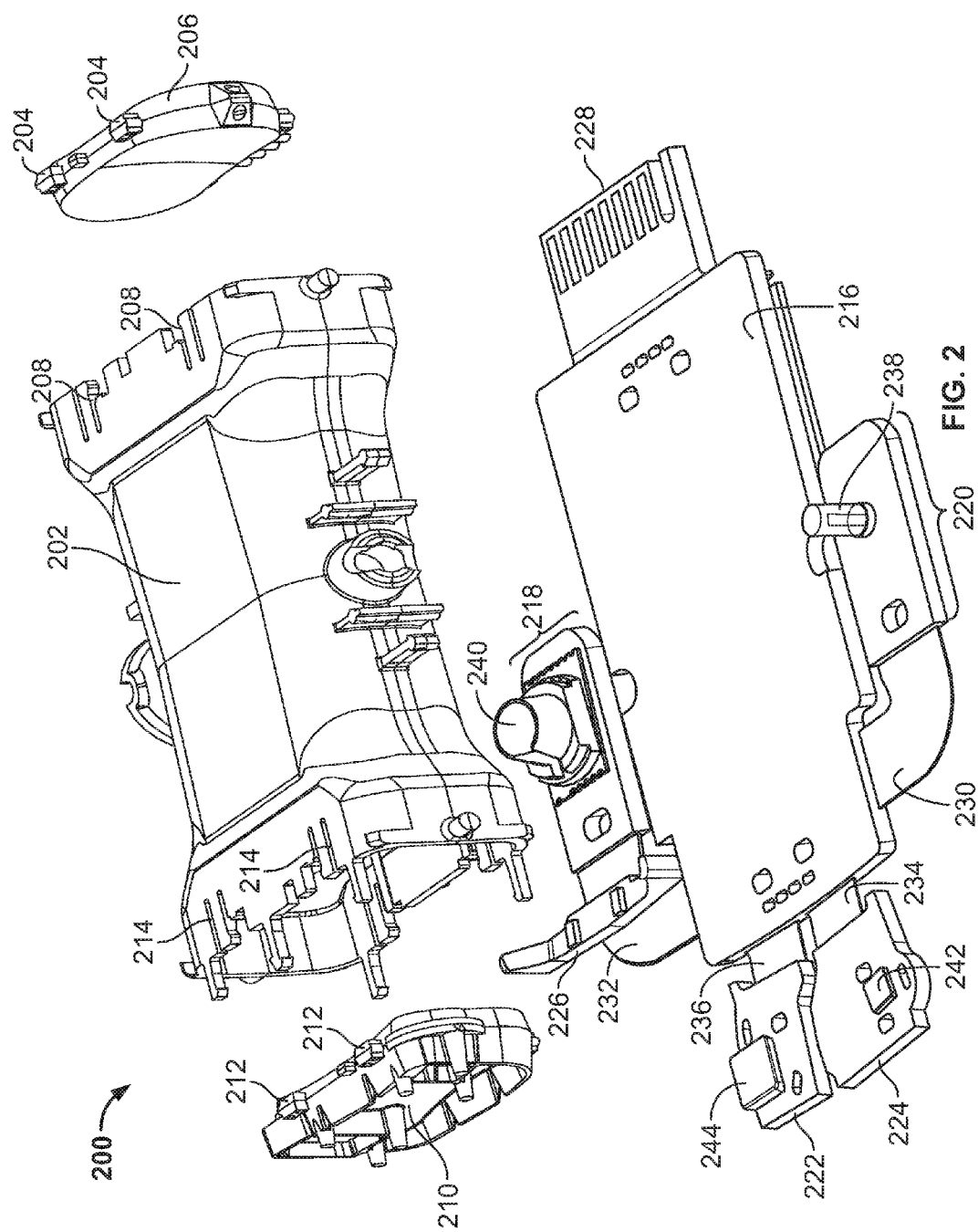
FIG. 2 depicts a perspective view showing the relative spatial relations of two mirrors, a backplane surface and first and second emitters and detectors of the breath sensor, according to an illustrative implementation.

FIG. 2 depicts a perspective view showing the relative spatial relations of two mirrors, a backplane surface and first and second emitters and detectors according to an illustrative implementation. The tube cell 202 enclosing the detection cavity includes notches 214 and 208 that allow easy connection and alignment of the mirrors 210 and 206 respectively. The notches allow the detection path between the emitters and the detectors to be maintained at a fixed and predefined alignment. Mirrors may be constructed of any metalized reflective surface and thermally stable material, such as epoxy. The notches 214 and 208 are complementary to the teeth 212 and 204 respectively. The tube cell 202 and mirrors 210 and 206 are then placed above a backplane surface 216. To reduce the footprint of the device, this backplane surface may house the central control circuitry, and would therefore be any surface capable of incorporating electrical circuitry. In an example, this backplane surface may be a PCB board. In the example shown, this surface may be in electrical communication with the mirrors 210 and 206. The heat generating and sensitive elements are located on separated, thermally isolated surfaces 218, 222, 224, 220 and 228. Surfaces 218, 222, 224, 220 and 228 may be PCB boards or any other surface capable of carrying electrical circuitry. Surface 218 is shown with a reference gas detector 240 mounted to the surface 218. In an example, this detector is a $CO_2$ infrared detector and the reference gas is $CO_2$. Surface 224 is also shown with a detector 242 mounted to the surface 224. In an implementation, detector 242 is selective of the absorption spectrum of a volatile substance of interest. The detectors 240 and 242 may be thermopile detectors of infrared radiation with bandpass interference filters tuned to the absorption peak of the substance to be detected or trace gas. The bandpass interval for an ethanol detector may be 9.1-9.9 μm, while the bandpass interval for an $CO_2$ detector may be 4.2-4.3 μm. The selectivity of the bandpass filters is typically performed by detecting ethanol with an optical bandpass filter specified by, for example, CWL=9.48 μm/FWHM=0.815 μm. This gives an approved selectivity against relevant potentially disturbing gases. Surfaces 218 and 224 thermally isolate the temperature-sensitive mounted detectors from heat generating regions of the breath sensor. Surfaces 218 and 224 include temperature regulating controls to maintain detectors 240 and 242 at an equilibrium temperature. These temperature regulating controls may be active heaters.

Surfaces 220 and 222 each have mounted electromagnetic emitters 238 and 244 respectively. In an example, 238 and 244 are infrared emitters 238 and 244 may be any standard electromagnetic source capable of producing infrared radiation. In an example, emitter 238 may be a blackbody radiating element such as a tungsten lamp that produces a beam of broadband infrared radiation. The emitters 238 and 244 may be modulated at a frequency above the frequency band of typical signals. Surfaces 220 and 222 thermally isolate the heat-generating emitters from heat sensitive regions of the breath sensor. Surfaces 220 and 222 include temperature regulating controls to maintain emitters 220 and 222 at an equilibrium temperature, thus providing stability for the output emissions wavelengths. These temperature regulating controls may be active heaters controlled by the backplane surface.

Surface 228 is an edge connector which provides an interface for manufacturing purposes and may be removed from the backplane surface 216. Surface 228 may be optionally replaced by another component such as a needle fixture in production. Surfaces 218, 220, 222 and 224 are each in electrical connection with the backplane surface 216. Surfaces 218, 220, 222 and 224 may be any surface capable of incorporating electrical circuitry, such as a PCB board. Surfaces 218, 220, 222 and 224 are in electrical connection with surface 216 via flexible connectors 232, 230, 236 and 234, respectively. These connectors 232, 230, 236 and 234 may be made from flex-film or other material and have low heat transfer between the PCBs. An additional component 226 secures the tube cell 202 and mirrors 210 and 206 to the backplane surface 216.

Figure 3:
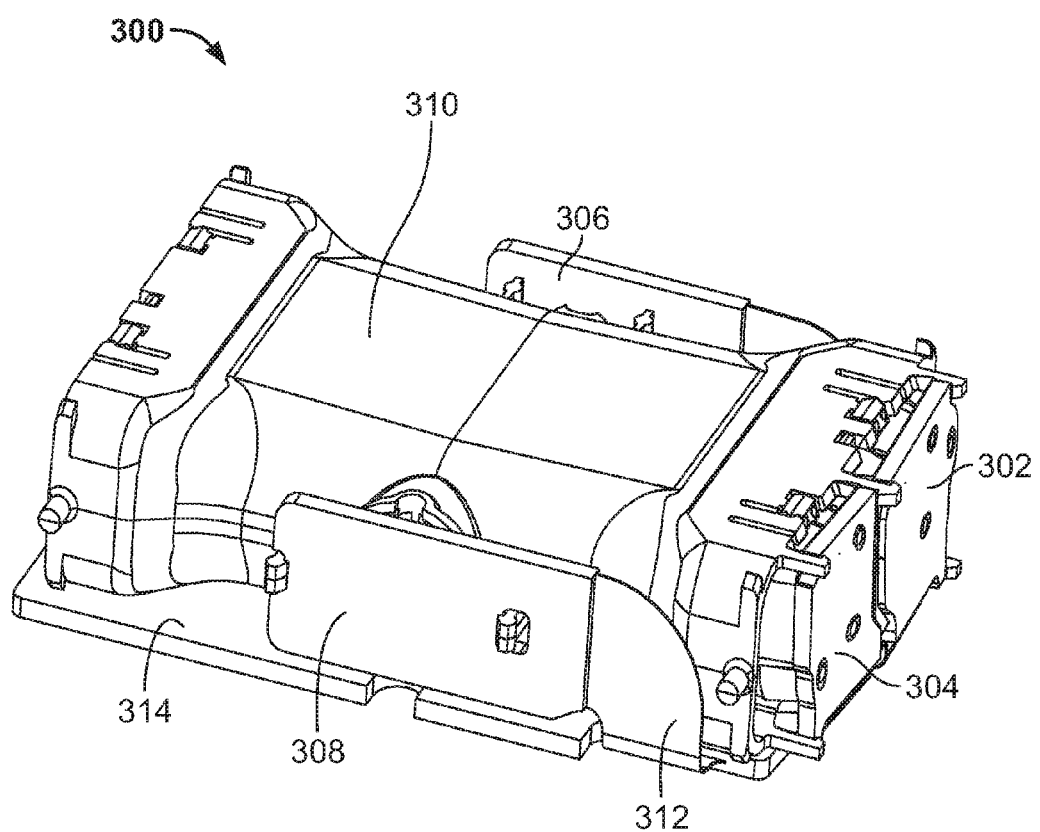
FIG. 3 depicts a perspective view of a tube cell and detection cavity, according to an illustrative implementation.

FIG. 3 depicts a perspective view showing the placement of heat generating and sensitive elements around a tube cell and detection cavity, according to an illustrative implementation. As shown in FIG. 3, the tube cell 310 is mounted on the backplane surface 314. Heat sensitive elements 308 and 302 containing detectors are shown wrapped around the body of the tube cell 310. Heat generating elements 306 and 304 containing emitters are also shown wrapped around the body of the tube cell 310. This is made possible by flexible electrical connectors such as 312 shown. Distributing elements 302, 304, 306 and 308 across the body of the tube cell 310 improves the thermal stability of the breath sensor, as well as avoiding interaction of the heat sensitive elements 308 and 302 with heat generating elements 306 and 304.

Figure 4:
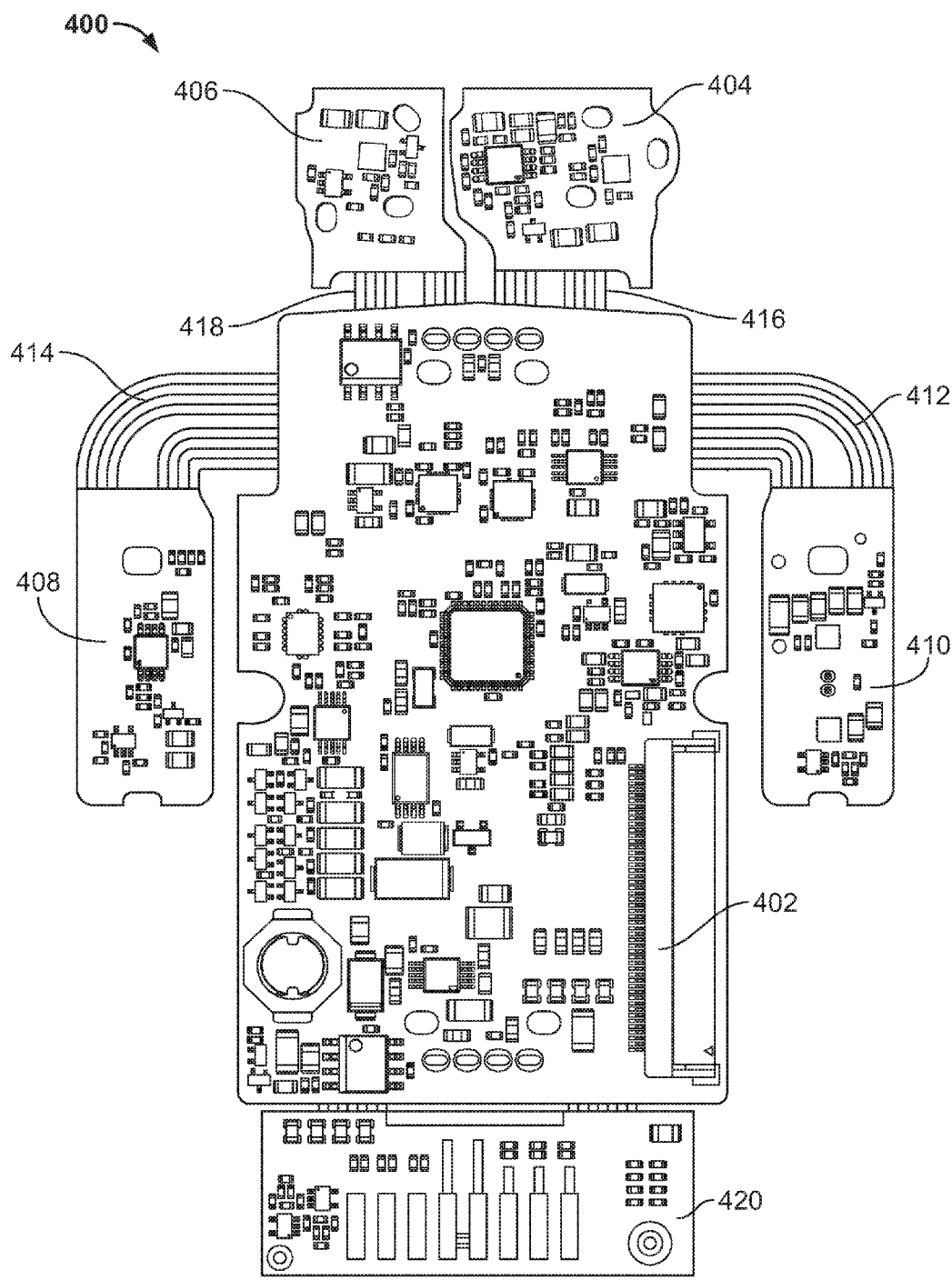
FIG. 4 depicts thermally isolated emitters and detectors in electrical connection with a backplane surface, according to an illustrative implementation.

FIG. 4 depicts thermally isolated emitters and detectors in electrical connection with a backplane surface, according to an illustrative implementation. The backplane surface may include additional temperature-regulating circuits placed strategically to reduce the overall thermal gradient of the breath sensor and to bring the breath sensor to a thermal equilibrium. These temperature-regulating circuits may be heaters, such that the equilibrium temperature of the breath sensor is substantially higher than the temperature of outside air. This allows single-direction heating control, reducing the complexity and start up time of temperature regulating circuits.

Surfaces 406 and 410 house mounted detectors, and are shown with schematic circuitry. Surfaces 408 and 404 house mounted emitters, and are also shown with schematic circuitry. The flexible electrical connections 414, 418, 416 and 412 are shown in signal communication between the backplane surface 402 and the thermally isolated surfaces 408, 406, 404 and 410 respectively. Surfaces 408, 406, 404 and 410 may be temperature regulated by the backplane surface 402 through the flexible electrical connections 414, 418, 416 and 412.

Figure 5:
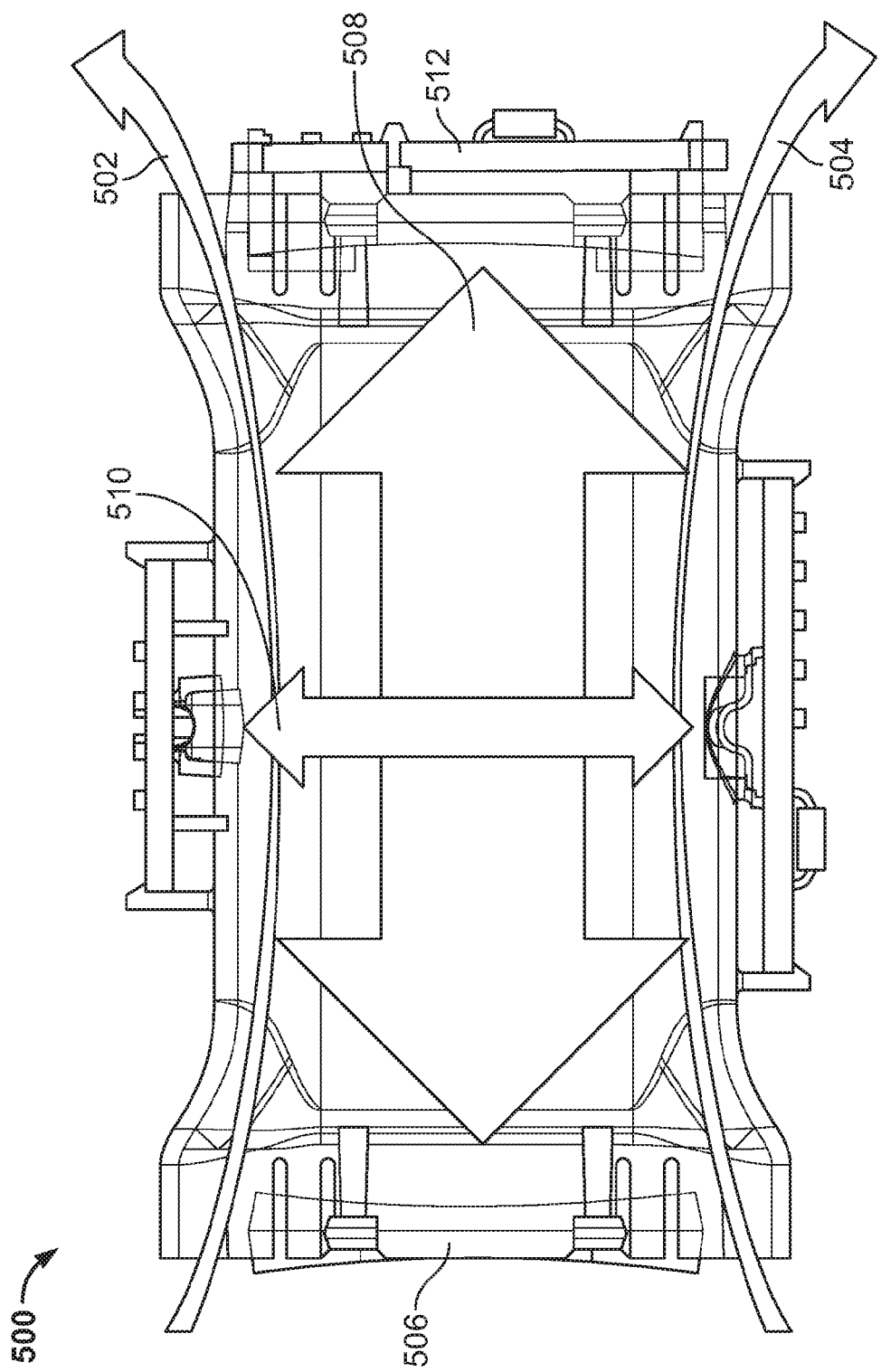
FIG. 5 depicts a first and a second detection path in relation to the airflow through the detection cavity, according to an illustrative implementation.

FIG. 5 depicts a first and a second detection path in relation to the airflow through the detection cavity, according to an illustrative implementation.

The measuring principle of this implementation is to use carbon dioxide ($CO_2$) as a tracer gas to indicate the degree of dilution of breath in ambient air.

Normal concentration of $CO_2$ in ambient air is approximately 400 parts per million or 0.04%. End tidal $CO_2$ concentration is both known and predictable, and is approximately 4.1 kPA according to active exhalation studies in the average human population. Thus, by measuring both $CO_2$ and alcohol through detection paths 510 and 508, the degree of dilution can be compensated for by using a mathematical algorithm. This algorithm may be the ratio between the measured concentrations of $CO_2$ and alcohol indicated by signals produced in detection paths 510 and 508, together with the known value of $CO_2$ in alveolar air, which will provide the alveolar air alcohol concentration.

The first detection path 510 is shown across the shorter dimension of the detection cavity. The first detection path 510 generates a first signal based on the concentration of a reference gas in the air flow shown as 502 and 504, circulating from the inlet 506 to the outlet 512. In an implementation, the reference gas is $CO_2$. Air flow 502 and 504 may optionally be forced by a fan. The first detection path 510 is path of electromagnetic radiation across the laminar flow of air 502 and 504. In an example, the electromagnetic radiation is infrared light and the first detection path is an optical path. The first signal may be an amplitude or any other electrical signal indicating absorption of the infrared light by the air flow 502 and 504.

The second detection path 508 generates a second signal based on the concentration of a volatile substance in the air flow shown as 502 and 504. In one implementation, this volatile substance is ethanol. The second signal path is a path of electromagnetic radiation in the direction of laminar flow of air 502 and 504. In one embodiment, the electromagnetic radiation is infrared light and the second detection path is an optical path. The second signal may be an amplitude or any other electrical signal indicated absorption of the infrared light by the air flow 502 and 504. The path length of the second detection path is several times that of the dimension of the detection cavity due to mirrors placed at either end of the detection cavity that reflect the infrared light before it becomes incident on the detector.

The optical path length of the first detection path may be shorter than the path length of the second detection path without sacrificing accuracy. $CO_2$ concentrations in expired air are much higher than that of most volatile substances, and thus to achieve a strong signal, the first detection path may not require additional reflection. This allows for the footprint of the breath sensor to be considerably compact and more easily integrated into a vehicle.

This measuring principle as described in FIG. 3 may be used for any combination of a tracer gas and a volatile substance of interest, and is not limited to $CO_2$ and alcohol. $H_2O$ may be an alternative to $CO_2$ as a tracer gas, or temperature sensing of the air flow may also be used as an indicator of breath dilution. Acetone, acetaldehyde, methyl alcohol, carbon monoxide, methane, ethane, propane, pentane, hexane, heptane, octane, isoprene, ammonia, hydrogen sulfide, methyl mercaptan, ethyl acetate, dimethyl ether, diethyl ether, benzene, toluene, methyl ethyl ketone, and methyl isobutyl ketone are examples of volatile substances that may be of interest from a diagnostic or toxicological perspective.

Figure 6:
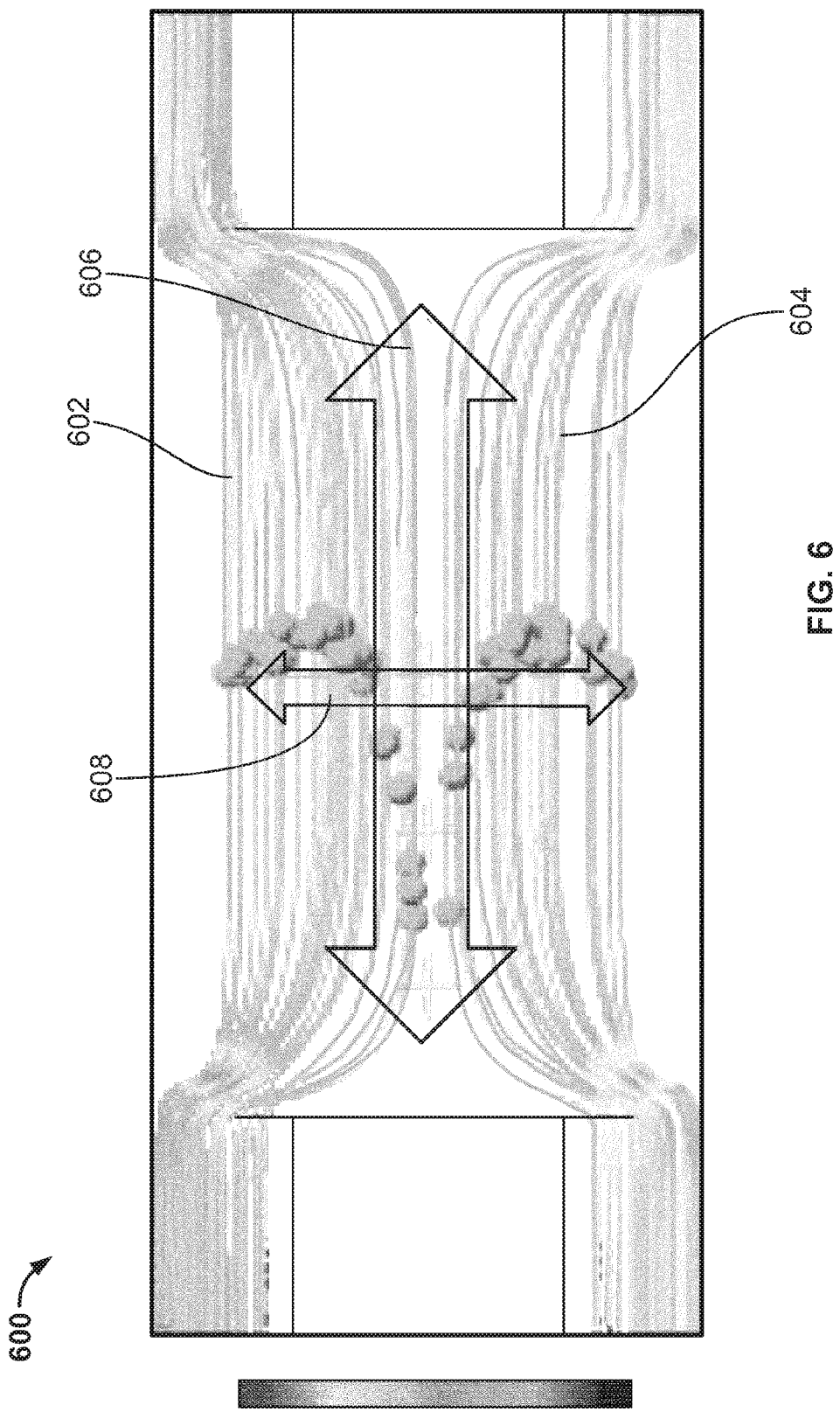
FIG. 6 depicts a simulation of the laminar flow of air through the detection cavity, according to an illustrative implementation.

FIG. 6 depicts a simulation of the laminar flow of air through the detection cavity, according to an illustrative implementation. The first detection path 608 and the second detection path 606 are shown as being perpendicular, but they also could be collinear, or arranged at another angle, as long as the two different optical paths are superimposed in the cell space and fill the same spatial air volume. Having a perpendicular or collinear arrangement of detection paths 606 and 608 allows having a shorter $CO_2$ detection path and a longer detection path for a volatile substance, such as EtOH, which may achieve improved measurement accuracy and speed. The laminar flow of air through the detection cavity 602 is designed such that the first signal and the second signal generated from the first detection path 608 and the second detection path 606 are substantially simultaneous. This is achieved through the relative spatial placement of the first detection path 608 and the second detection path 606, as well as the optional active flow of air via a fan. The simultaneous signals ensure that the measured dilution factor of a reference gas corresponds to the measured volatile substance concentration, thus improving accuracy of the device.

Figure 7:
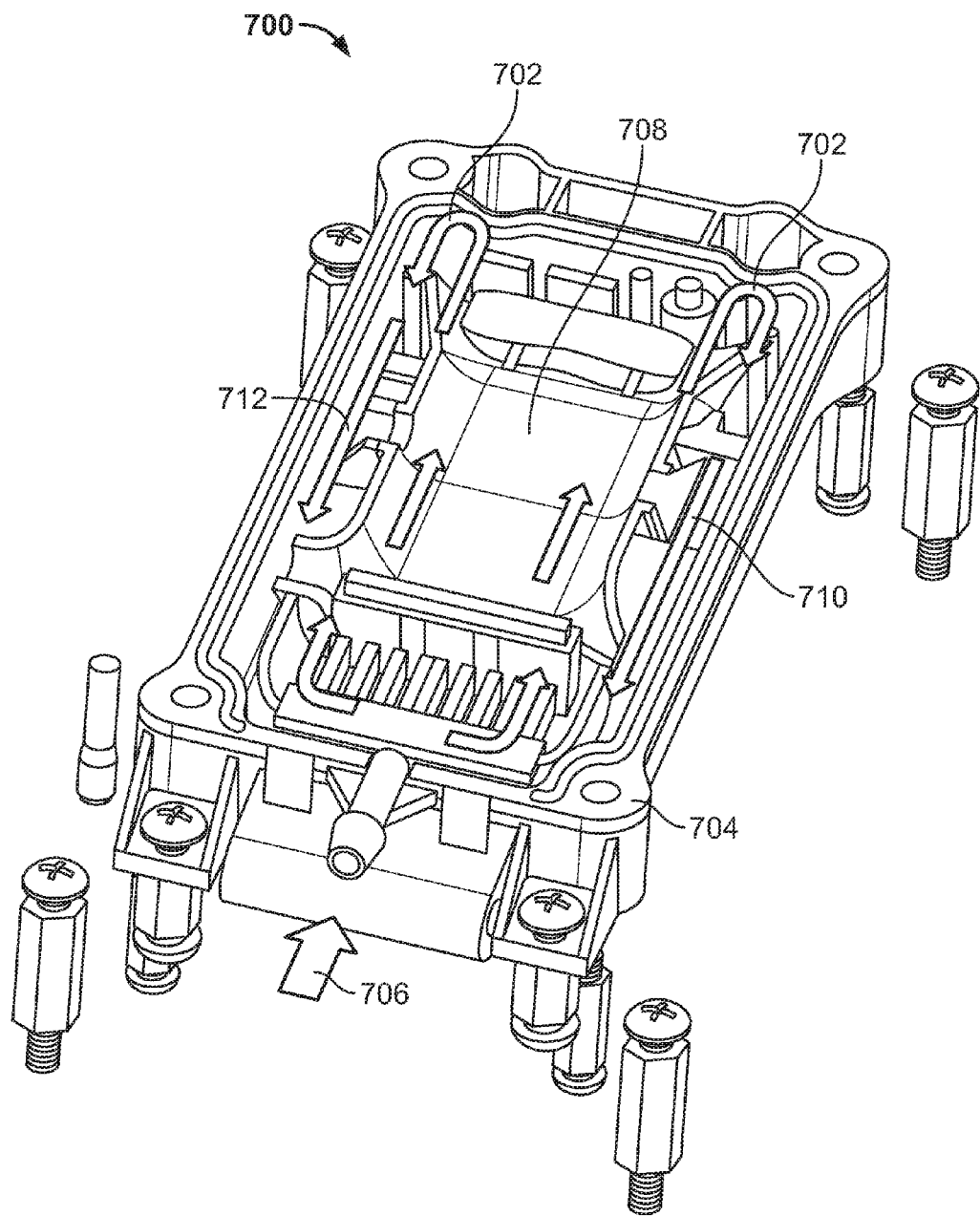
FIG. 7 depicts a perspective view of the breath sensor with recirculated air flow, according to an illustrative implementation.

FIG. 7 depicts a perspective view of an embodiment of the present invention with recirculated air flow, according to an illustrative implementation. In this embodiment, air enters the detection cavity 708 via an inlet 706. An additional housing case 704 encloses the detection breath sensor such that there is a gap between the external wall of the tube cell and the interior wall of the housing case, as shown as 710. At the end of the detection cavity, air is then re-directed back over the body of the detection cavity, as shown as 702 and 712. The re-circulated air may then exit the housing case at the same end as the inlet 706, or in any other orientation that may encourage air flow out of the detection cavity and through the gap between the housing case and tube cell. This additional housing case increases thermal stability of the breath sensor by providing a thermal shield between the detection cavity and its outside environment. This reduction in thermal gradient specifically on either side of the walls of the tube cell additionally reduces geometric deformations of the tube cell and the optical path lengths of the first and second detection paths. The temperature difference between the gap and the detection cavity is dependent on the outside ambient temperature difference and is typically in the range of a fraction of a degree Celsius.

Figure 8:
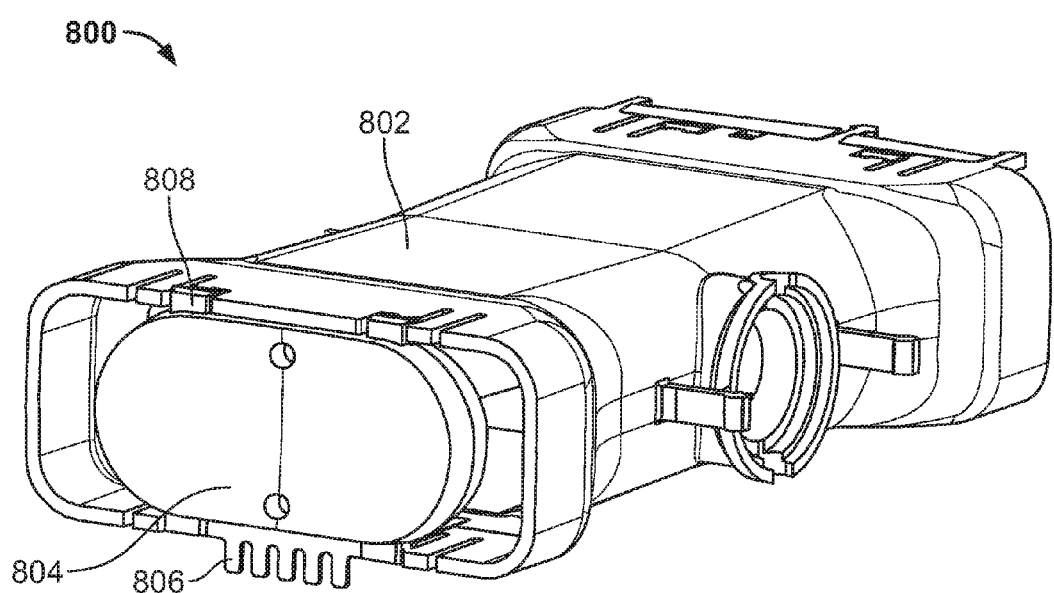
FIG. 8 depicts a perspective view of an interface between a mirror and the tube cell, with teeth built in to the mirror, according to an illustrative implementation.

FIG. 8 depicts a perspective view of an interface between a mirror and the tube cell, with teeth built in to the mirror, according to an illustrative implementation. The mirror 804 includes teeth 806 for securing to a backplane surface, as well as teeth 808 for securing to the tube cell 802. These teeth ensure alignment of the mirror with respect to the detection cavity. The mirror 804 may also be designed to have minimal mass to allow fast start up times and allow for better thermal control of its surface.

Figure 9:
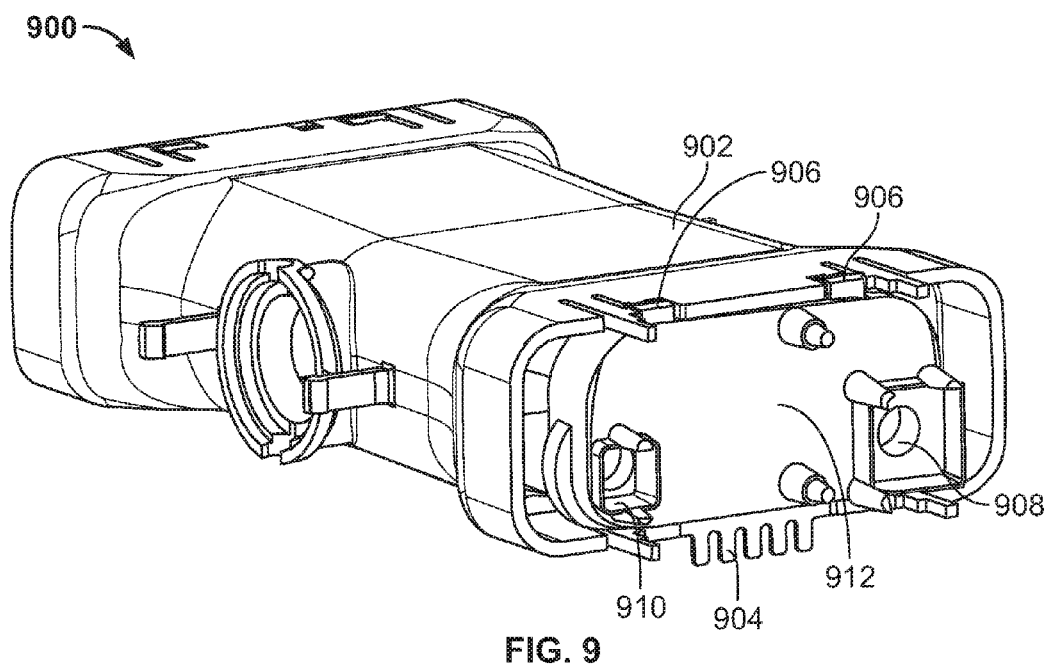
FIG. 9 depicts a perspective view of an interface between a second mirror and the tube cell, with teeth built in to the mirror, according to an illustrative implementation.

FIG. 9 depicts a perspective view of an interface between a second mirror and the tube cell, with teeth built in to the mirror, according to an illustrative implementation. The mirror 912 includes teeth 904 for securing to a backplane surface, as well as teeth 906 for securing to the tube cell 902. The mirror 912 is further configured to optically integrate a detector (through space 908) and an emitter (through space 910) such that the mirror may provide reflections of the infrared light between these two endpoints of the second detection path. Optically integrating the detector and emitter further allows for a compact design of the breath sensor.

FIG. 10 depicts two perspective views of a first mirror, two perspective views of a second mirror, and their relative positions to the tube cell in addition to built-in heating elements underneath the reflective surface of each mirror, according to an illustrative implementation. Heating elements 1002 and 1008 are shown, which are molded beneath the reflective surface of mirrors 1004 and 1009 respectively. These heating elements may be copper wires or any other material capable of behaving as a resistive heater or generating heat, and designed to prevent temperature gradients between the preheated air flow in the detection cavity and the reflective surfaces. If warm, moist expired breath comes into contact with cooler surfaces, water vapor in the air will condense on the mirror surfaces and disrupt the optical path of the second detection path. The heating elements 1002 and 1008 prevent condensation by heating the reflective surfaces of the mirrors 1004 and 1009 respectively, thus preventing cooling and condensation. Both mirrors are secured to opposite sides of the tube cell 1010, and are aligned such that their reflective surfaces are substantially parallel to each other.

FIG. 11 depicts a perspective view of a first mirror, according to an illustrative implementation. The side view 1100 of mirror 1102 shows curvature of the mirror, which allow the infrared light to be reflected between mirror 1004 and 1009 multiple times, before being focused on the detector located behind mirror 1009. The angle of curvature may be adjusted to increase or decrease the path length of this second detection path. FIG. 11 also illustrates that the mirror 1100 is designed with a symmetric cross-section such that there identical curvature on both sides, although only one side is used as a concave mirror. This arrangement adds environmental stability, and avoids "bi-metal" bending effects and asymmetric stress, that otherwise might deform the mirror curvature.

FIG. 12 depicts a perspective view of a connection between the mirrors and a backplane surface according to an illustrative implementation. Teeth 1216 connect to backplane surface 1214 such that mirror 1210 and mirror 1212 are essentially aligned. This alignment may be an optical alignment. The area 1202 between mirror 1210 and mirror 1212 is typically occupied by the tube cell 1308.

FIG. 13 depicts a perspective view of the connection between the mirrors, tube cell a backplane surface, according to an illustrative implementation. This perspective view shows below the backplane surface 1302, where the connection between the backplane surface 1302 and the tube cell 1308 is shown at 1310. Mirrors 1304 and 1306 are shown in alignment. Tube cell 1308 may provide exact alignment of the tube and mirror using precision tube and mirror connections.

FIG. 14 depicts a tooth connection between a mirror and a backplane surface, according to an illustrative implementation. This connection shows teeth 1402 connected to the backplane surface 1406 at the edge of the mirror 1408 and centered in the profile of the mirror 1404.

FIG. 15 depicts a cross section of a tooth connection between a mirror and a backplane surface, according to an illustrative implementation. The cross section shows the notches 1504 in the backplane surface 1502 such that the mirror 1506 is connected.

FIG. 16 depicts a perspective view of a mirror, according to an illustrative implementation. The mirror is curved at 1602. The curvature of this angle may be adjusted to the geometry of the breath sensor.

FIG. 17 depicts the distribution of a plurality of heating elements in a mirror, according to an illustrative implementation. These heating elements may be copper wires, or any other material capable of behaving as a resistive heater or generating heat. As shown in 1710, the heating elements 1708 and 1706 are not uniformly distributed over the mirror surface, and are instead concentrated at points of contact between the mirror and the tube cell (as seen at 1308). The mirror 1602 and tube cell 1308 are thus thermally coupled, and in order to equally distribute heat across the surface of the mirror, heating elements must be concentrated at these points to account for the additional mass of the tube cell. This means that at central points on the mirror, such as 1708, the heating elements may be more dispersed. The heating elements may be electrically separated so that they are subject to separate electrical controls, allowing fine tuning of the heat gradient across the mirror 1602's surface. The electrical connection of the plurality of heating elements may be at nodes located on the teeth, as shown at 1704. Each tooth may have its own separate electrical connection to the plurality of heating elements 1709 and 1706.

FIG. 18 depicts a perspective view of a mirror, according to an illustrative implementation. Mirror 1816 contains optical integration for detectors and emitters, shown at 1812 and 1814.

FIG. 19 depicts the distribution of a plurality of heating elements in a mirror, according to an illustrative implementation. These heating elements may be copper wires, or any other material capable of behaving as a resistive heater or generating heat. As shown in 1924, the heating elements 1922 and 1920 are not uniformly distributed over the mirror surface, and are instead concentrated at points of contact between the mirror and the tube cell (as seen at 1308). The mirror 1816 and tube cell 1308 are thus thermally coupled, and in order to equally distribute heat across the surface of the mirror, heating elements must be concentrated at these points to account for the additional mass of the tube cell. This means that at central points on the mirror, such as 1922, the heating elements may be more dispersed. The heating elements may be electrically separated so that they are subject to separate electrical controls, allowing fine tuning of the heat gradient across the mirror 1816's surface. Mirror 1224 additionally has concentrations of heating elements shown at 1920 around holes in the mirror, shown as 1812 and 1814. These account for additional masses for coupling the reference gas detector and emitter to the mirror 1816. It is possible to design multiple distributions of the heating elements, however this is an example implementation given the relation of the mirrors to the tube cell. Different sections of the heating elements may be separately controlled with feedback circuitry in communication with the backplane surface. This would allow for finer control of the temperature on the surface of the mirrors. The connections between the heating elements and the backplane surface are shown as nodes located on the teeth 1918. The coupling of the mirror teeth with the backplane surface thus further serves as an electrical interface, in addition to a reliable and easy way of aligning the two mirrors.

Figure 20:
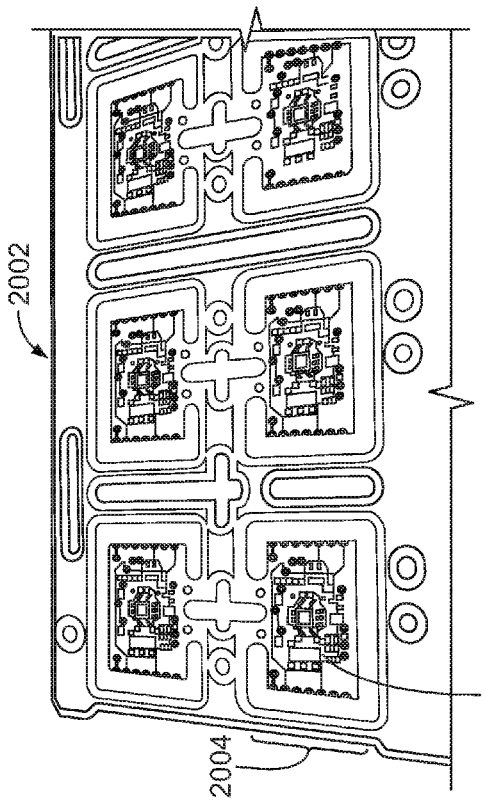
FIG. 20 depicts a step in manufacturing a reference gas detector, according to an illustrative implementation.

FIG. 20 depicts a step in manufacturing a reference gas detector, according to an illustrative implementation. In one implementation, the tracer gas detector is a $CO_2$ detector. The tracer gas detector 2308 includes preamplifier and interference filter circuits 2006, and other optional signal filtering circuits shown at 2004 to further select for the absorption peak of the tracer gas. This circuitry may be assembled as at 2002.

Figure 21:
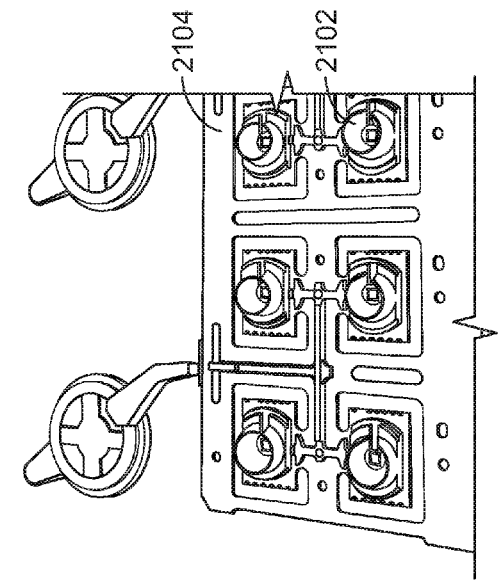
FIG. 21 depicts a step in manufacturing a reference gas detector, according to an illustrative implementation.

FIG. 21 depicts a step in manufacturing a reference gas detector, according to an illustrative implementation. In this step, the detectors 2102 shown at 2002 are then placed in a mold 2104 into which epoxy or another thermally ideal material is poured. The surface of the epoxy is then metalized to allow for the reflection of incident light on the detector.

Figure 22:
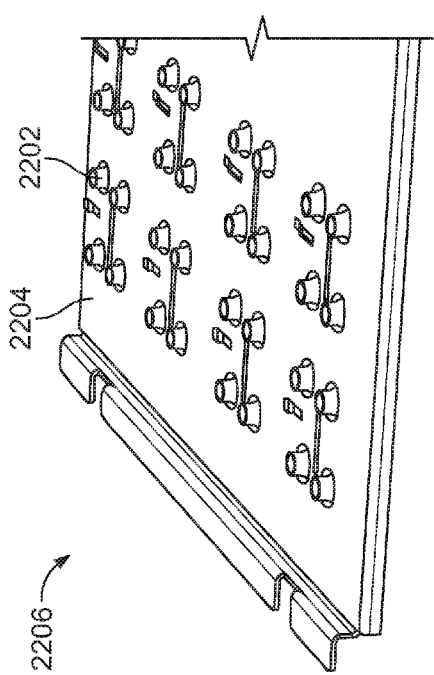
FIG. 22 depicts a step in manufacturing a reference gas detector, according to an illustrative implementation.

FIG. 22 depicts a step in manufacturing a reference gas detector. In this step 2206, to protect the circuitry components shown at 2002, a shadow mask 2204 is applied at 2206 before metallization.

Figure 23:
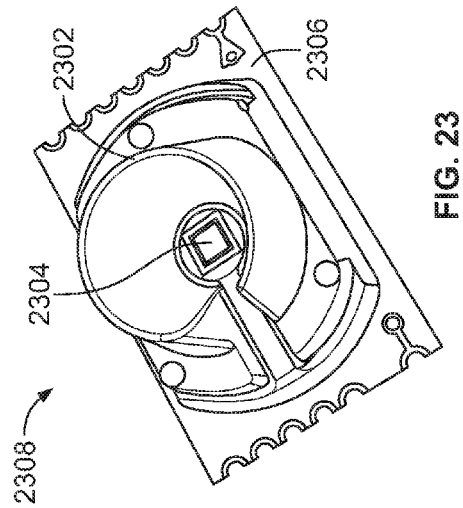
FIG. 23 depicts a completed reference gas detector, according to an illustrative implementation.

FIG. 23 depicts a completed reference gas detector, according to an illustrative implementation. The complete tracer gas detector is shown at 2308. An interference filter 2304 is shown layered over the detector, which is located directly below it. The collection hood 2302 is shown as a curved, reflective surface surrounding the detector. Since the path length of the tracer gas (e.g. $CO_2$) is relatively short to allow for a more compact footprint of the breath sensor, and the corresponding emitter is a broad spectrum light source, the collection hood 2302 is added to the tracer gas detector to focus incident light over the detector, thus improving signal to noise of the $CO_2$ concentration signal. The collection hood 2302 also helps to shield the detector from other light sources in the detection cavity.

FIG. 24 depicts a cross sectional view of a volatile substance detector into a mirror 2402, according to an illustrative implementation. The detector 2406 is located below a protective window 2404. The detector 2406 is surrounded by thermally stabilized material, such as an epoxy material, in all directions, such that the thermal gradient over the detector is substantially zero. The backplane surface 2408 is also thermally stabilized and isolated from heat-generating elements of the breath sensor. This interface between the detector, detection cavity 2410, and tube cell 2412 improves the signal to noise ratio of the absorption signal of the volatile substance of interest.

Figure 25:
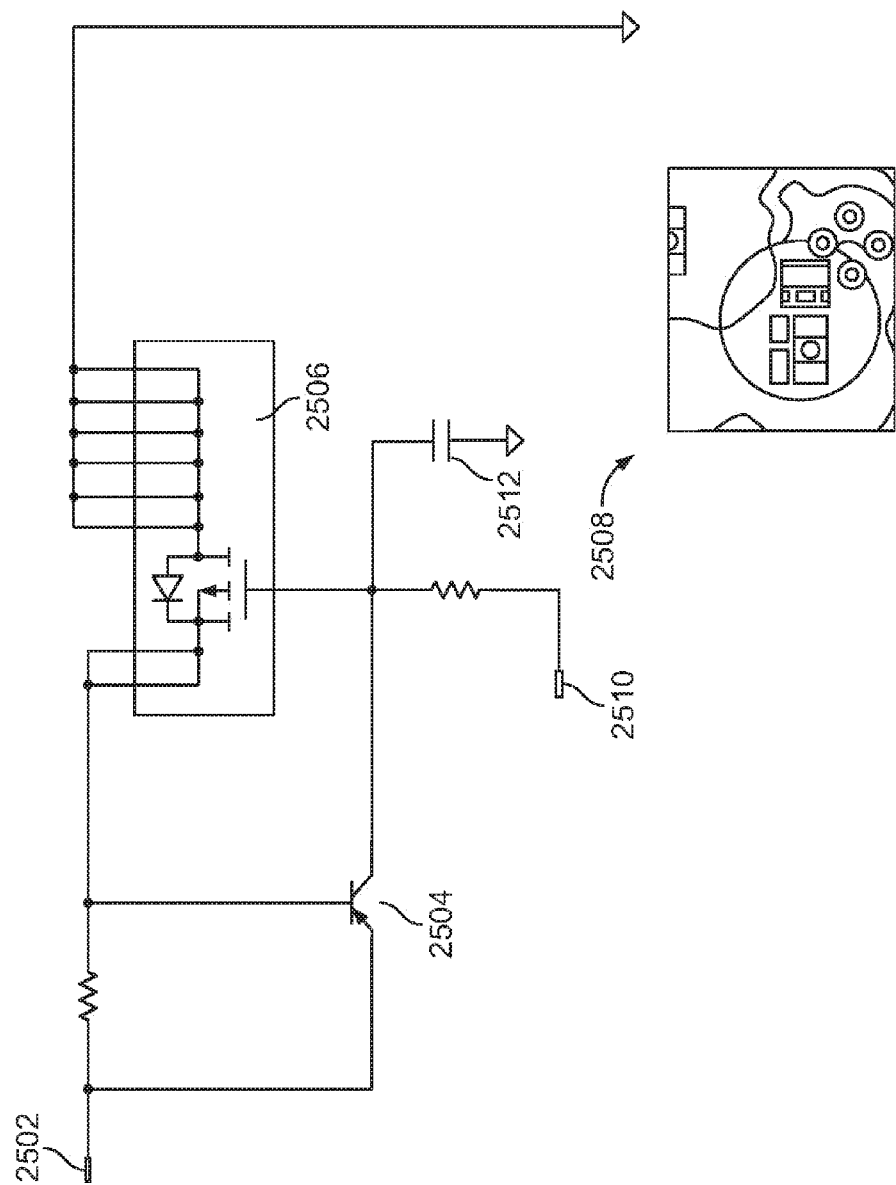
FIG. 25 depicts a transistor heater used to heat detectors and light sources, according to an illustrative implementation.

FIG. 25 depicts a transistor heater used to heat a detector, according to an illustrative implementation. This transistor heater includes an electrical power input 2502, control signal input 2510 and transistors 2504 and 2506. The input 2510 is connected to a control signal, which may be a voltage or a current. These transistors may be any commercially available transistors. This circuit is more effective with much lower delays than a resistive heater for heat injection into a ground plane, decreases power dependence on power input voltage and reduces the footprint of the heater for the reference gas detector, and is shown printed on a PCB surface in 2508. The heating circuit 2508 is in signal communication with logic on the backplane surface. The capacitor 2512 is an optional slew rate limiter. This non-traditional heating circuit meets size constraints on the reference gas detector surface.

Figure 26:
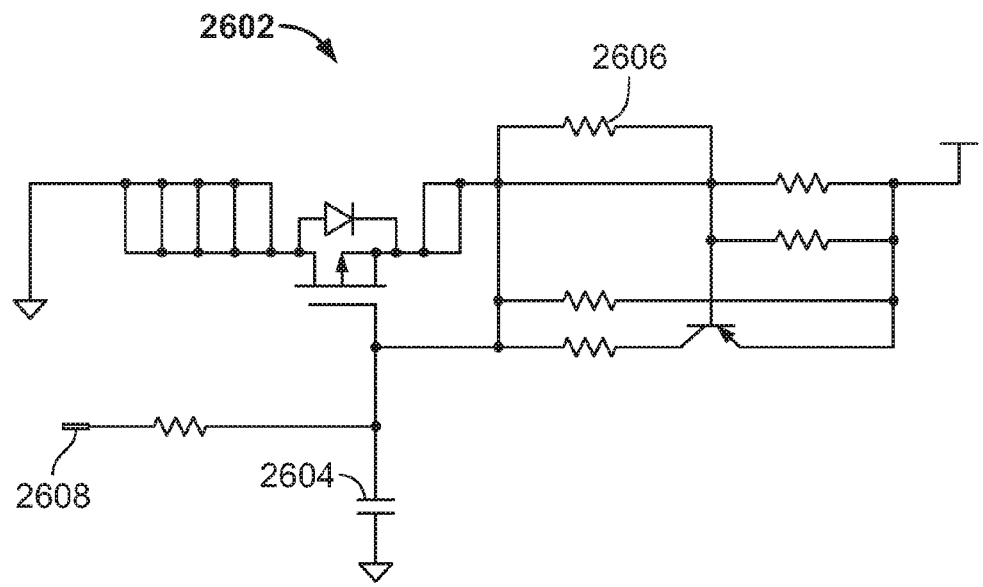
FIG. 26 depicts an optional additional heater control circuit, according to an illustrative implementation.

FIG. 26 depicts a transistor heater with an optional additional heater control circuit, according to an illustrative implementation. This circuit 2602 may be connected to circuit 2508 at the input 2510. This circuit includes hardware overheating protection at 2606, in addition to a slew rate limiter at 2604. The input to the heater circuit may be at 2608. All resistors, capacitors, diodes and other electrical circuitry may be standard electrical components.

Figure 27:
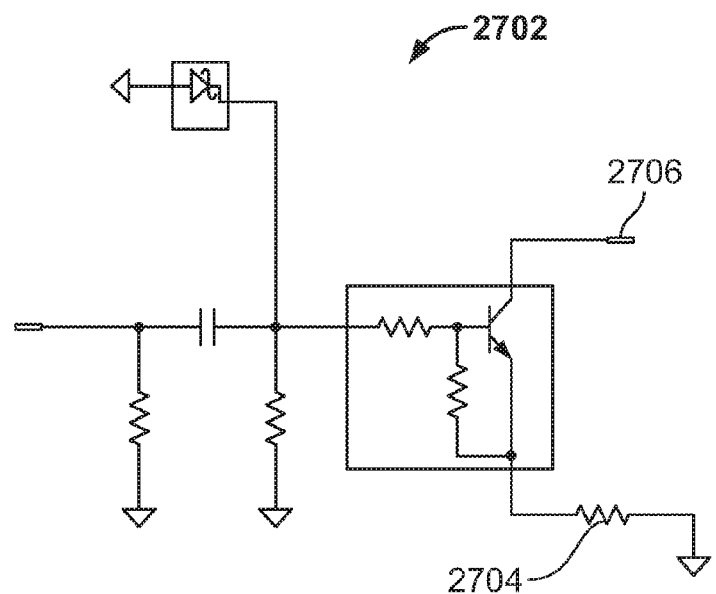
FIG. 27 depicts an optional additional heater control circuit, according to an illustrative implementation.

FIG. 27 depicts an optional additional heater control circuit, according to an illustrative implementation. This circuit 2702 may be connected to circuit 2508 at the input 2510, and may be added separately or in conjunction with circuit 2602. This circuit includes a resistor 2704 which allows the circuit 2508 to be controlled by a current. The output to the heater circuit may be at 2706. All resistors, capacitors, diodes and other electrical circuitry may be standard electrical components.

Figure 28:
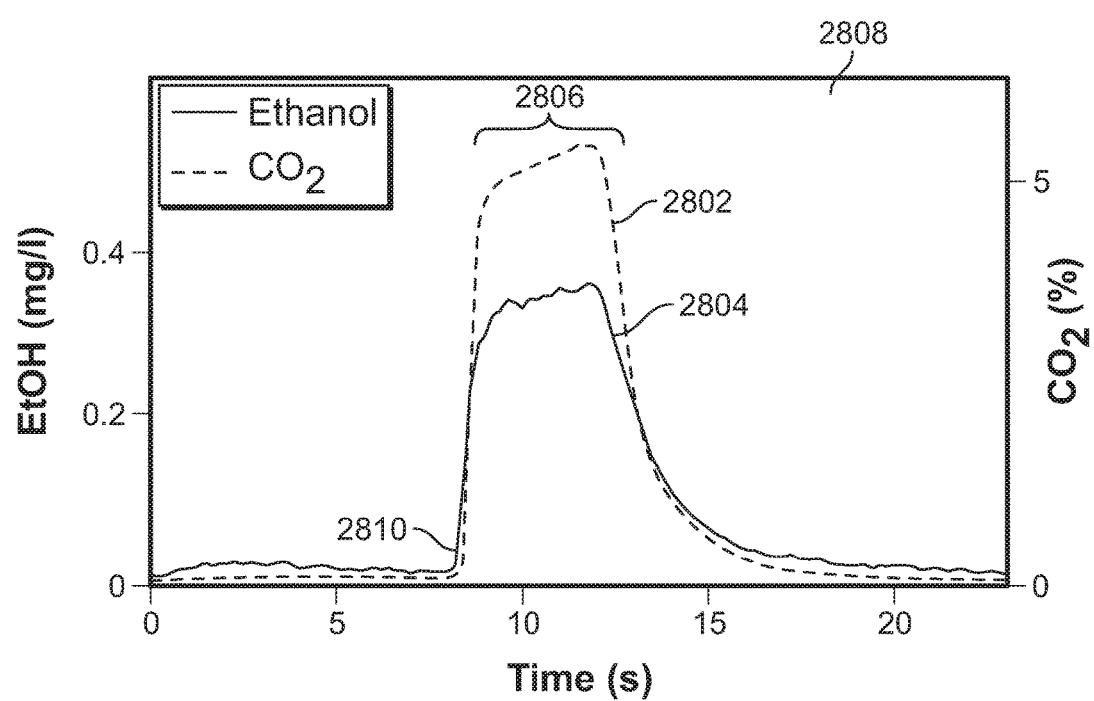
FIG. 28 depicts experimental results of the signal response from a breath test, according to an illustrative implementation.

FIG. 28 depicts experimental results of the signal response from a breath test, according to an illustrative implementation. The curve 2802 represents an example signal in response to the presence of a reference gas, which in the diagram 2808 is shown to be $CO_2$. The curve 2804 represents an example signal in response to the presence of a volatile substance, which in the diagram 2808 is shown to be ethanol. The time duration of the two signals, shown at 2806, is similar. The first response to the presence of the reference gas and volatile substance shown at 2810 is within a fraction of a second. Thus the two signals are substantially concurrent such that the difference in their response time is very close to zero. In an example, the ethanol response curve may be slightly ahead of the $CO_2$ curve, as shown at 2810, as the latter comes from deeper levels of the lung. This difference may not be practically detected and is shown here as an example.

Figure 29:
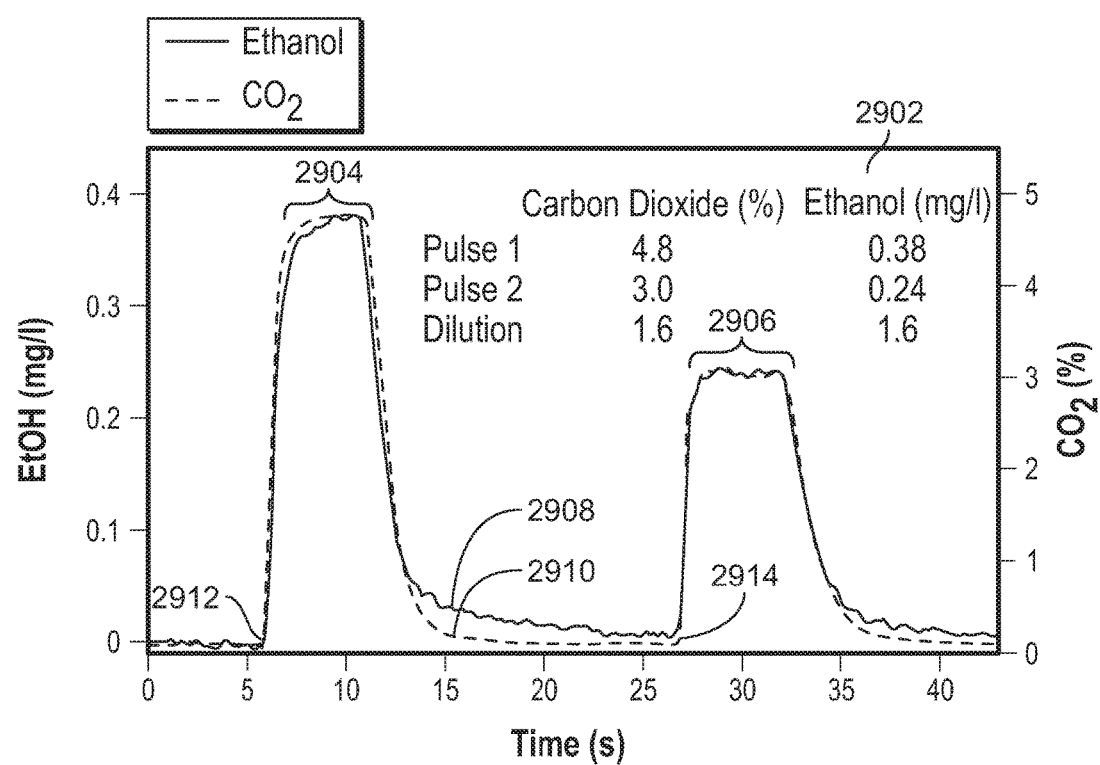
FIG. 29 depicts the experimental results of signal response to gas pulses, according to an illustrative implementation.

FIG. 29 depicts the experimental results of signal response to gas pulses, according to an illustrative implementation. These results show signal responses at two different distances from a breath sensor. Pulse 2904 is the result of breath exhaled at 0 cm from an air inlet, while pulse 2906 is the result of breath exhaled at 5 cm from an air inlet. The volatile substance shown at 2903 is ethanol, while the reference gas detected is shown to be $CO_2$. These two pulses 2904 and 2906 show the volatile substance signal 2908 as closely tracking the reference gas signal 2910. The two signals are also shown at 2912 and 2914 to respond substantially simultaneously to the gas pulses.

All components defining optical performance and path length could be manufactured by a stable compound according to U.S. patent application Ser. No. 14/362,384, filed Jun. 2, 2014, which is incorporated by reference herein.

It will be understood that the foregoing is only illustrative of the principles of the invention, and that the invention can be practiced by other than the described embodiments, which are presented for purposes of illustration and not of limitation, and the present invention is limited only by the claims which follow.

What is claimed is:

1. A breath test system comprising:
   an air inlet configured to receive an air flow for a breath sample;
   a detection cavity connected to the air inlet in which the air flow circulates, the detection cavity comprising:
      a first electromagnetic detection path configured to generate a first signal based on the presence of a reference gas in the air flow, and
      a second electromagnetic detection path configured to generate a second signal based on the presence of a volatile substance in the air flow, wherein the first electromagnetic detection path is thermally isolated from the second electromagnetic detection path; and
   logic in signal communication with the first detection path and the second detection path configured to determine a concentration of the volatile substance in the air flow based on the first signal and the second signal.

2. The breath test system of claim 1, wherein the first electromagnetic detection path comprises a first electromagnetic emitter and a first electromagnetic detector, and the second electromagnetic detection path comprises a second electromagnetic emitter and a second electromagnetic detector and wherein:

the first electromagnetic emitter and the second electromagnetic emitter produce infrared light; and the first electromagnetic detector and the second electromagnetic detector are infrared detectors.

3. The breath test system of claim 2, wherein the first electromagnetic emitter, the first electromagnetic detector, the second electromagnetic emitter and the second electromagnetic detector are each thermally isolated.

4. The breath test system of claim 3, wherein the logic is further configured to maintain the system at a predetermined operating temperature different from a temperature outside of the detection cavity.

5. The breath test system of claim 4, wherein:
the system operates in an environment having an ambient temperature that ranges from about −40° C. to about 85° C.; and
the predetermined operating temperature is greater than ambient temperature.

6. The breath test system of claim 5, wherein the predetermined operating temperature is greater than 45° C.

7. The breath test system of claim 3, wherein the second detection path further includes a first mirror and a second mirror configured such that an effective path length of the infrared light is longer than any linear dimension of the detection cavity.

8. The breath test system of claim 7, wherein the first signal and the second signal are generated respectively by the first electromagnetic detector and the second electromagnetic detector simultaneously.

9. The breath test system of claim 8, wherein the first mirror and the second mirror each include a plurality of heating elements molded beneath a reflective surface of the first mirror and the second mirror; and
the plurality of heating elements are distributed across the first mirror and the second mirror such that a net thermal gradient of the first mirror and the second mirror is minimized.

10. The breath test system of claim 9, wherein the plurality of heating elements on the first mirror and the second mirror are in signal communication with the logic, and are adjusted such that there is no condensation on the reflective surface of each of the first mirror and the second mirror.

11. The breath test system of claim 10, wherein the first electromagnetic detector comprises an integrated preamplifier, an integrated heater, an interference filter, and a collection hood, wherein the collection hood is substantially reflective and curved to focus such that incident electromagnetic radiation from the first electromagnetic emitter is focused towards the first electromagnetic detector.

12. The breath test system of claim 11, further comprising a shielding housing enclosing the detection cavity, the shielding housing arranged, such that a gap exists between the exterior of the detection cavity and the shielding housing, and wherein the air flow circulates from the detection cavity into the gap.

13. The breath test system of claim 2, wherein:
the first electromagnetic detector is selective of an infrared absorption frequency of the reference gas; and
the second electromagnetic detector is selective of an infrared absorption frequency of the volatile substance.

14. The breath test system of claim 1 wherein the second electromagnetic detection path is substantially perpendicular to the first detection path.

15. The breath test system of claim 1 wherein the second electromagnetic detection path is substantially collinear to the first detection path.

16. A breath test system, comprising:
an air inlet configured to receive an air flow for a breath sample;
a detection cavity connected to the inlet in which the air flow circulates, the detection cavity comprising a detection path defined by a dimension of the detection cavity and configured to generate a first signal based on the presence of a volatile substance in the air flow;
a shielding housing enclosing the detection cavity, the shielding housing arranged such that a gap exists between the detection cavity and the shielding housing;
an air circulator, such that the air flow circulates through the gap; and
logic in signal communication with the detection path and configured to determine a concentration of the volatile substance in the air flow based on the first signal.

17. The breath test system of claim 16, wherein the air circulator is a fan configured to circulate the air flow through the detection cavity and the gap.

18. The breath test system of claim 17, wherein the air circulator is in signal communication with the logic, and the logic is configured to adjust the velocity of the air flow.

19. The breath test system of claim 18, wherein the air inlet further comprises a preheater configured to adjust the air flow to a predetermined operating temperature, and a temperature of the gap is the predetermined operating temperature.

20. The breath test system of claim 19, wherein the predetermined operating temperature is different than the temperature outside of the shielding housing.

21. The breath test system of claim 20, wherein:
the system operates in an environment having an ambient temperature that ranges from about −40° C. to about 85° C.; and
the predetermined operating temperature is greater than ambient temperature.

22. The breath test system of claim 21, wherein the predetermined operating temperature is greater than 45° C.

23. The breath test system of claim 20, wherein the detection path is an electromagnetic path, and comprises a first electromagnetic emitter and a first electromagnetic detector.

24. The breath test system of claim 23, wherein the electromagnetic path further comprises a first mirror and a second mirror, and is configured such that an effective path length of the electromagnetic radiation is longer than any linear dimension of the detection cavity.

25. The breath test system of claim 24, wherein the detection cavity further comprises a second electromagnetic signal path that generates a second signal, and wherein the logic is further configured to determine the concentration of the volatile substance based on a first signal and a second signal.

26. The breath test system of claim 25, wherein the first signal and the second signal are generated simultaneously.

27. A breath test apparatus, comprising:
a backplane surface;
a first mirror connected to the backplane surface;
a second mirror connected to the backplane surface, wherein the connection between the second mirror and the backplane surface optically aligns the first mirror with the second mirror;
a tube cell connected to the first mirror and the second mirror, wherein the tube cell defines a detection cavity for measuring a concentration of a volatile substance; and a first optical path oriented across a first dimension of the tube cell, and wherein the first optical path, the first mirror and the second mirror are in electrical communication with the backplane surface.

28. The breath test apparatus of claim 27, wherein the backplane surface includes a plurality of temperature controlling circuits distributed such that the optical path and the detection cavity are substantially maintained at a thermal equilibrium.

29. The breath test apparatus of claim 27, wherein the first mirror and the second mirror each include a plurality of heating elements molded beneath a reflective surface of the first mirror and the second mirror, and wherein the backplane surface is in electrical communication with the plurality of heating elements.

30. The breath test apparatus of claim 29, wherein the first mirror and the second mirror are connected to the backplane surface with complementary teeth and notches, and the complementary teeth and notches provide electrical connection between the backplane surface and the first mirror.

31. The breath test apparatus of claim 30, wherein a first set of heating elements in the plurality of heating elements of the first mirror is in separate electrical communication with the backplane surface from a second set of heating elements in the plurality of heating elements of the first mirror, and wherein the separate electrical communication is achieved through separate teeth and notches.

32. The breath test apparatus of claim 27, wherein the first optical path comprises a first electromagnetic detector and a first electromagnetic emitter, and the first electromagnetic detector and first electromagnetic emitter are optically incorporated into the first mirror.

33. The breath test apparatus of claim 32, wherein the first electromagnetic detector and the second electromagnetic detector each contain heating elements, and wherein the heating elements are controlled by the backplane surface.

34. The breath test apparatus of claim 32, further comprising a second optical path oriented across a second dimension of the tube cell.

35. The breath test system of claim 32, wherein the first electromagnetic detector comprises an integrated preamplifier, an integrated heater, an interference filter, and a collection hood, wherein the collection hood is substantially reflective and curved such that incident electromagnetic radiation from the first electromagnetic emitter is focused towards the first electromagnetic detector.

36. The breath test apparatus of claim 27, wherein the backplane surface is in signal communication with an exterior processing unit, and is configured to send a result of a determination of the concentration of the volatile substance in the detection cavity to the exterior processing unit.

37. A method for testing breath, comprising:
receiving, at an air inlet, an air flow for a breath sample;
circulating, into a detection cavity connected to the air inlet, the air flow for a breath sample;
generating a first signal in a first electromagnetic detection path based on the presence of a reference gas in the air flow;
generating a second signal in a second electromagnetic detection path based on the presence of a volatile substance in the air flow;
generating a third signal based on the first signal and the second signal, wherein the third signal represents a concentration of the volatile substance in the air flow based on the first signal and the second signal;
thermally isolating, in a backplane surface, the first electromagnetic detection path from the second electromagnetic detection path;
maintaining a thermal equilibrium of the first electromagnetic detection path and the second electromagnetic detection path; and
determining, at logic in signal communication with the first electromagnetic detection path and the second electromagnetic detection path, a concentration of the volatile substance in the air flow from the third signal.

38. The method of claim 37, wherein maintaining the thermal equilibrium comprises maintaining the first electromagnetic detection path and the second electromagnetic detection path at temperatures substantially different from a temperature outside of the detection cavity.

39. The breath test method of claim 37 wherein the second electromagnetic detection path is substantially perpendicular to the first detection path.

40. The breath test method of claim 37 wherein the second electromagnetic detection path is substantially collinear to the first detection path.

41. A method for testing breath, comprising:
receiving, at an air inlet, an air flow for a breath sample;
circulating, into a detection cavity connected to the inlet, the air flow for a breath sample;
generating a first signal in a detection path defined by a dimension of the detection cavity and based on the presence of a volatile substance in the air flow;
shielding the detection cavity such that a gap exists between the detection cavity and a shielding housing;
circulating the air flow through the gap; and
determining, at logic in signal communication with the detection path, a concentration of the volatile substance in the air flow based on the first signal.

42. The method for testing breath of claim 41, further comprising circulating the air flow through the gap with a fan.

43. The method for testing breath of claim 42, wherein circulating the air flow includes adjusting the velocity of the air flow.

44. The method for testing breath of claim 43, wherein receiving the air flow further comprises preheating the air flow to a predetermined operating temperature different than the temperature outside of the shielding housing.

45. The method for testing breath of claim 41, further comprising generating a second signal, and wherein determining the concentration of the volatile substance is based on the first signal and the second signal.

46. The method for testing breath of claim 45, wherein generating the first signal and generating the second signal occurs simultaneously.

* * * * *